United States Patent [19]

Rüegg

[11] 4,157,716

[45] Jun. 12, 1979

[54] APPARATUS FOR THE DOSED DISPENSING OF A LIQUID

[75] Inventor: André Rüegg, Zürich, Switzerland

[73] Assignee: Contraves AG, Zürich, Switzerland

[21] Appl. No.: 874,466

[22] Filed: Feb. 2, 1978

[30] Foreign Application Priority Data

Mar. 7, 1977 [CH] Switzerland ............... 2777/77

[51] Int. Cl.² ............................................. A61M 5/20
[52] U.S. Cl. ........................... 128/218 A; 128/DIG. 1
[58] Field of Search ........... 128/218 A, 218 C, 218 R, 128/213, 214 E, 214 F, DIG. 1, 215; 222/14–22

[56] References Cited

U.S. PATENT DOCUMENTS

| 2,627,270 | 2/1953 | Glass ............................... 128/218 A |
| 3,812,843 | 5/1974 | Wootten et al. ............. 128/DIG. 1 |
| 3,858,581 | 1/1975 | Kamen ........................... 128/218 A |
| 4,059,110 | 11/1977 | Wuthrich et al. ............. 128/218 A |

Primary Examiner—John D. Yasko

Attorney, Agent, or Firm—Herbert Cohen; Werner W. Kleeman

[57] ABSTRACT

An apparatus for the dosed dispensing of a liquid by means of an injection device equipped with a motor-driven spindle mechanism, a cylinder and a piston, one end of the piston being axially displaceable in the cylinder and the other end being operatively connected with one end of a spindle shaft of the spindle mechanism. At the opposite end of the spindle shaft there is provided a first scale ring connected with the spindleshaft and a second scale ring which engages with the first scale ring. A coupling element connects the second scale ring with an adjustment device, the second scale ring being rotatable and thus adjustable with respect to the first scale ring by axially disengaging or declutching the same. Both of the scale rings are equipped with at least one stop means for limiting the adjustment path of the second scale ring for setting the volume of the liquid to be dispensed or dosed.

11 Claims, 3 Drawing Figures

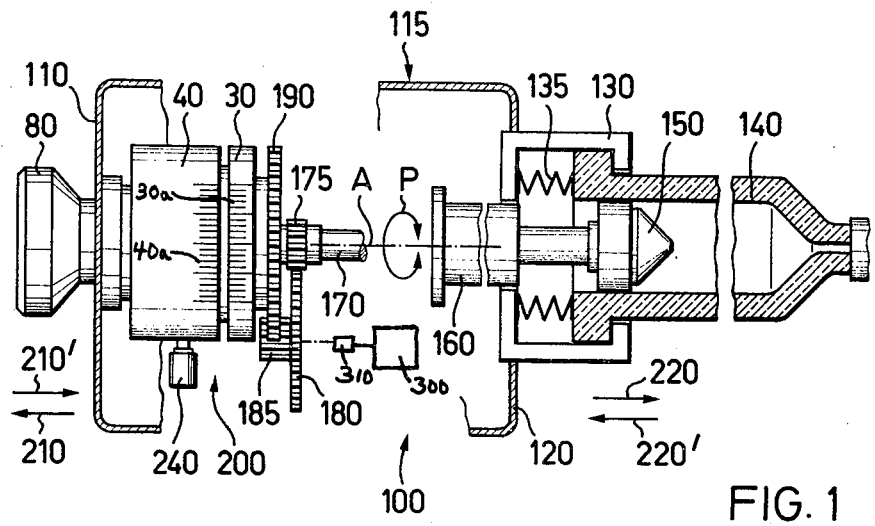
FIG. 1
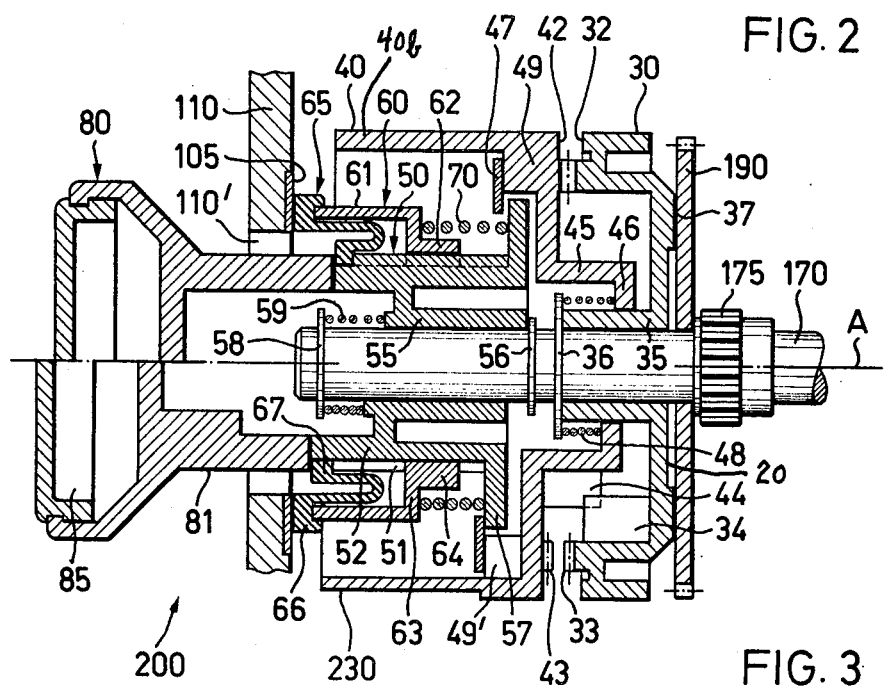
FIG. 2
FIG. 3

APPARATUS FOR THE DOSED DISPENSING OF A LIQUID

BACKGROUND OF THE INVENTION

The present invention relates to a new and improved construction of apparatus for the dosed dispensing of a liquid by means of an injection device, typically a syringe, which apparatus is of the type generally comprising a motor-driven spindle mechanism including a spindle shaft, a cylinder, and a piston or piston arrangement, the piston or piston arrangement being mounted to be axially displaceable with one end thereof within the cylinder and connected at its other end with the spindle shaft.

In order to inject liquids, such as for instance X-ray contrast agents into the blood vessels of living bodies or organisms, there is already known to the art an injection device essentially composed of an electric motor having a gearing drive or transmission, a spindle mechanism and a magnetic coupling. By means of switching disks appropriately arranged within the apparatus housing it is possible to operate a traction cable or the like connected with the drive spindle. The switching disks are used for pre-selecting the volume of the liquid to be injected, for monitoring the volume of such liquid as well as for providing electrical contact with further external devices. These switching disks are operated by operating knobs arranged at the housing of the apparatus. Further details of such prior art dispensing apparatus are contained in "Bulletin des schweizerischen elektronischen Vereins," Volume 1, February 1969, Nr. 3, Pages 103–107.

SUMMARY OF THE INVENTION

It is a primary object of the present invention to provide a new and improved construction of apparatus for the dosed dispensing of a liquid in an extremely reliable and efficient manner.

Still a further significant object of the present invention aims at the provision of an apparatus for the dosed dispensing of a liquid, the apparatus being intended to coact with an injection device for dispensing the liquid and which injection device can be actuated by a spindle mechanism, such apparatus being structured to ensure for a positive, uniform control of a predetermined quantity of the liquid to be injected, while preventing any unintentional false resetting of the apparatus which would undesirably alter such controlled dispensing.

In keeping with the immediately preceding object, it is a further aim of the invention to provide an apparatus of the aforementioned type which, especially, satisfies prescribed safety requirements regarding the amount of liquid to be dispensed, typically in the medical field, and furthermore, affords both a space-saving arrangement while possessing a construction which is relatively simple both from the aspect of assembly and maintenance of the apparatus.

Yet a further significant object of the present invention is directed to a new and improved construction of apparatus for the dosed dispensing of a liquid in an accurate, reliable and positive manner, enabling setting of the desired volume or quantity of liquid to be dispensed, without danger of unintentional improper resetting of the set volume to be dispensed, and which apparatus is extremely easy to use, economical to manufacture, highly reliable in operation, not readily subject to malfunction or breakdown, and requires a minimum of maintenance and servicing.

Another significant object of the present invention is concerned with apparatus for dispensing a liquid, particularly but not exclusively in the medical field, such as liquids intended for injection into the blood vessels of a living organism, wherein the apparatus is structured so that there can be positively, rapidly and easily set a desired quantity of liquid to be dispensed, without the danger of inadvertent false resetting of the once set volume, and where setting of the desired volume can be accomplished most easily, without the need to carry out complicated or extensive manipulations.

Now in order to implement these and still further objects of the invention, which will become more readily apparent as the description proceeds, the apparatus for the dosed dispensing of a liquid is generally manifested by the features that:

(a) a first scale element, typically in the form of a scale ring is connected with the other end of the spindle shaft remote from the piston or piston arrangement and a second scale element, again typically a scale ring, operatively engages with the first scale ring;

(b) the second scale ring is connected by means of a coupling element with an adjustment device, such as an adjustment knob or grip, and can be rotated and thus adjusted in relation to the first scale ring by axially declutching or disengaging such second scale ring; and (c) both of the scale rings have at least one respective stop means for the purpose of limiting the adjustment path of the second scale ring for the volume adjustment, i.e., setting of the desired volume or quantity of liquid to be dispensed.

The apparatus of this development ensures for an exact course of the control of the liquid dispensing operation, and therefore, affords, when used in the medical field, an exact dispensing of the liquid to be injected in a volume or dosage as prescribed by the attending doctor and important to the life functions of the patient. The set volume cannot be altered except by axially declutching or disengaging the second scale ring which is coupled with the adjustment grip or the like. Hence, there is beneficially prevented any unintentional false setting of a once properly set dosage, for instance by inadvertently contacting the adjustment grip. Moreover, the setting of the dosage or volume of the liquid which is to be dispensed can only be accomplished as a function of the volume of liquid which is present in the cylinder, which liquid typically may be a contrast agent for injection into the blood vessels of a human body or other living organism. Additionally, the apparatus is optimally sealed towards its environs due to a specially constructed and arranged seal or sealing device.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a partial schematic view of an injection device equipped with apparatus for the dosed dispensing of a liquid and constructed according to the teachings of the present invention;

FIG. 2 shows in sectional view and on an enlarged scale the dosage controlled-dispensing apparatus of FIG. 1 in its engaged or clutched position; and FIG. 3 illustrates the apparatus as shown in FIG. 2, but this time with the parts thereof shown in the disengaged or declutched position.

DETAILED DESCRIPTION OF THE PREFERRED EMBODIMENTS

Describing now the drawings, in FIG. 1 there is schematically illustrated part of an injection device 100. There will be recognized an apparatus housing 115 having a front housing wall 120 and a rear housing wall 110. At the front housing wall 120 there is arranged holder means 130 which can be affixed by a suitable, conventional means, not here further shown, at the housing 115. The holder means 130 serves for receiving a cylinder 140. This cylinder 140 is insertable into the holder or holder means 130 and can be positioned with the aid of spring elements 135 under spring force in such holder means 130. The cylinder 140 may comprise part of a standard syringe for injecting liquids into blood vessels of living bodies. By way of example, a syringe useful with the dispensing apparatus of the invention has been disclosed in the commonly assigned, U.S. Pat. No. 4,030,496, granted June 21, 1977, entitled "Syringe for Injecting Liquids into Blood Vessels of Living Bodies", to which reference may be readily had and the disclosure of which is incorporated herein by reference. Obviously, other suitable syringe constructions can be used, as can also any other suitable injection device for dispensing a liquid.

Within the cylinder 140 there is arranged a piston or piston member 150 which is operatively connected with a plunger 160, as best seen by referring to FIG. 1. The plunger 160 together with the therewith connected piston or piston member 150 can be operated by a spindle mechanism embodying a spindle shaft 170, such that the piston or piston arrangement 150 selectively reciprocates in the cylinder 140 in the direction of the arrows 220 and 220', respectively. The spindle shaft 170 is driven to rotate about the lengthwise axis A in the direction of the double-headed arrow P by means of a schematically illustrated electric motor or other suitable drive 300 which is operatively connected with the spindle shaft 170 by any suitable gearing, which therefore simply has been generally indicated by reference character 310.

As best seen by further referring to FIG. 1, the spindle shaft 170 contains a pinion 175 meshing with a gear 180. Arranged at the gear 180 is a further pinion 185 which meshes with a further gear 190.

To obtain a dosed dispensing of a liquid there is arranged within the apparatus housing 115 an appropriately constructed apparatus or device 200 connected by means of the gear 190 with the spindle shaft 170 and therefore operatively connected with the remaining, previously discussed drive elements 310, 300. By means of the apparatus 200, there can be controlled the movement of the piston or piston arrangement 150 in the direction of the arrow 220, and thus the dosed dispensing of the liquid.

Now in FIGS. 2 and 3 there have been illustrated on an enlarged scale and in sectional view, the apparatus 200. The upper half of the apparatus as shown in FIG. 2 illustrates the parts in the clutched or engaged position, and the lower half of the apparatus, as shown in FIG. 3, illustrates the parts in the declutched or disengaged position.

This apparatus 200 will be seen to essentially comprise a first scale element, here in the form of a scale ring 30, a second scale element, likewise in the form of a scale ring 40, a coupling element 50, a sliding sleeve 60, seal means, here in the form of a roll seal 65, and adjustment means, here shown as an adjustment grip or handle or knob 80 equipped with a cover member 85. Both of the scale rings 30 and 40 in the clutched or engaged position of the apparatus 200, as shown in FIG. 2, are operatively connected with one another at their confronting end faces or sides by suitable means, such as the teeth 33, 43 as will be discussed more fully hereinafter. In FIGS. 2 and 3, there has been illustrated an advantageous, weight-saving construction of the previously discussed parts, and which will be described more fully hereinafter.

The scale ring 30 is provided at its one face 20 with a substantially ring-shaped or annular surface 37 which comes into contact with the gear 190 which is fixed by any suitable fixing means, not particularly here shown. At the other oppositely situated side or face 32 this scale ring 30 has force transmitting means in the form of entrainment elements, here preferably shown as a radial toothed gear or radially extending teeth 33. By means of its hub 35, the scale ring 30 can be mounted upon the spindle shaft 170 and positively fixed by a securing or safety ring 36 or equivalent structure. Additionally, this scale ring 30 is provided with at least one stop or impact means 34, arranged within such ring 30, as best seen by referring to the lower right-hand portion of FIG. 3.

Continuing, as to the other scale ring 40, the same is provided at the face or side 42 thereof which confronts the face or side 32 of the first scale ring 30 also with complimentary entrainment means, here in the form of a radial toothed gear or radially extending teeth 43 matching the radial toothed gear or radially extending teeth 33 of the first scale ring 30. The scale ring 40 which is constructed in the form of a sleeve 40b is preferably configured in a step-like fashion, i.e. stepped, and will be seen to comprise, among other things, a substantially cylindrical hub 45 embodying a ring-shaped flange 46 which is centered at the outer surface of the hub 35 of the first scale ring 30 and guided to be axially displaceable. Between the flange 46 and the securing ring 36 there is arranged a compression or pressure spring 48, under the action of which both of the scale rings 30 and 40 are held in operative engagement with one another at their confronting end faces or sides 32 and 42, respectively. Furthermore, within the scale ring 40 there are arranged in distributed fashion about the circumference thereof the cams 49 for increasing the strength of the scale ring 40 and also the cams 49' with which there comes into contact a coupling disk 47 which is fixedly connected by any suitable means with such scale ring 40. Analogous to the stop means 34 of the first scale ring 30, the second scale ring 40 also is provided with an impact member or stop means 44.

The coupling element 50 will be seen to comprise a substantially cylindrical part 52 having grooves 51 distributively arranged at its outer circumference, a substantially ring-shaped flange 57 which is directed towards the outside and merges with the cylindrical part 52, and also a cylindrical hub 55. By means of the hub 55, the coupling element 50 is axially displaceably mounted upon the spindle shaft 170 and the movement of the coupling element 50 towards the one side is limited by a securing or safety ring 56 and towards the other, oppositely situated side by means of a further securing or safety ring 58 as well as by the action of a compression or pressure spring 59 interposed between the securing ring 58 and the confronting end of the hub 55.

The sliding sleeve 60 will be seen to comprise a cylindrical part 61 and a hub portion or hub 62. The cylindrical part 61 and the hub portion 62 are interconnected by a substantially ring-shaped flange 63. The hub or hub portion 62 is equipped with resilient cams 64 or equivalent structure in a corresponding arrangement to that of the grooves 51 of the coupling element or member 50. The sliding or displaceable sleeve 60 is axially displaceably guided against the force of a pressure spring 70 which bears at the flange 63 and at the flange 57 and is rigidly connected for rotation with the coupling element 50 by means of the spring or resilient cams 64.

The roll seal 65 comprises an outer ring bead or protruberance 66 and an inner ring bead or protruberance 67. This roll seal 65 is urged by means of the ring bead 66, which is operatively connected with the cylindrical part 61 of the sliding sleeve 60, against a slide or friction disk 105 arranged at the inside of the housing wall 110, whereas the inner ring bead is pressed against the coupling element 50 by the action of the cylindrical part 81 of the adjustment knob 80 or other suitable adjustment means. The adjustment knob or grip 80, which can be closed by means of the cover 85, and extends through the opening 110' of the housing wall 110, is fixedly connected in any suitable fashion with the coupling element 50 such as by threading, fastening screws, bonding, or the like.

Having now had the benefit of the foregoing discussion of the apparatus for the dosed dispensing of a liquid, the mode of operation thereof will be described in conjunction with the injection device, and is as follows:

After placement of the liquid-filled cylinder 140 in the holder or holder means 130, there is set by means of the apparatus 200 the volume or quantity of liquid which is to be controllably dispensed or dosed. To this end, at the region of the apparatus 200 there is provided at the top of the housing 115 a not particularly illustrated but standard calibrated plate having a window and a marking line or marker. Both of the scale rings 30 and 40 are appropriately arranged with respect to the graduated plate, and each of these scale rings 30 and 40 have a respective scale-division, as partially shown in FIG. 1, related to the marking line or marker of the graduated plate. The first scale ring 30 indicates by means of its scale 30a, which is related to the marking line or marker of the graduated plate, the volume of quantity of liquid contained within the dispensing cylinder 140, whereas the scale 40a of the second scale ring 40 beneficially serves for adjusting the quantity of liquid which is to be dispensed by axially displacing such second scale ring, i.e. declutching the same, in the direction of the arrow 210 with respect to the first scale ring 30.

During the injection operation, at which time the dispensing piston or piston arrangement 150 arranged in the dispensing cylinder 140 is moved in the direction of the arrow 220, both of the operatively interconnected scale rings 30 and 40 are rotated in such a manner about the axis A in the direction of the arrow P until the scale ring 40 which is equipped with an appropriately structured switching element or tab 230 actuates a terminal switch 240. This, in turn, causes the drive unit 300 to turn-off and thus stopping the dispensing operation.

If there is still present an adequate quantity of liquid in the cylinder 140 — which can be readily ascertained by easily reading the position of the scale 30a of the scale ring 30 in relation to the marker or marking line at the graduating plate — then, when necessary, there can be easily accomplished a further injection operation. To this end, by axially retracting the adjustment knob in the direction of the arrow 210 — the flange 57 of the coupling element 50 then comes into engagement with the coupling disk 47 and both of the scale rings 30 and 40 are out of engagement with one another — it is possible by rotating the adjustment or setting handle or knob 80 and the scale ring 40 to set in relation to the scale ring 30 a further quantity of liquid which is to be dispensed. By releasing the adjustment knob or grip 80, such is shifted by the force of the spring 70 in the direction of the arrow 210', and at the same time both of the scale rings 30 and 40 are brought into operative engagement with one another. Now there can be accomplished a further injection operation.

In order to fill the dispensing cylinder 140, the dispensing piston or piston arrangement 150 is moved in the direction of the arrow 220', whereafter when the piston or piston arrangement 150 has reached a predetermined position, it is then possible to remove the cylinder 140 together with the piston or piston arrangement 150 out of the holder means 130.

While there are shown and described present preferred embodiments of the invention, it is to be distinctly understood that the invention is not limited thereto, but may be otherwise variously embodied and practiced within the scope of the following claims. Accordingly,

What I claim is:

1. An apparatus for the dosed dispensing of a liquid by means of an injection device, comprising:
   a motor-driven spindle mechanism including a spindle shaft;
   a dispensing cylinder for the liquid;
   a dispensing piston arrangement axially displaceable at one end thereof in the dispensing cylinder;
   said dispensing piston arrangement being operatively connected at its other end with one end of said spindle shaft;
   a first scale means connected with the other end of said spindle shaft;
   a second scale means cooperating with said first scale means;
   said first scale means and said second scale means being structured for operable interengagement with one another;
   a coupling element;
   adjustment means including an adjustment element operatively connected by said coupling element with said second scale means for axially disengaging said second scale means from said first scale means by rotating said second scale means relative to said first scale means and thus positionally adjusting said second scale means in order to set a desired volume of liquid to be dispensed from said injection cylinder; and
   each of said scale means being provided with at least one stop means for limiting the path of adjustment of the second scale means during the setting of the volume of liquid which is to be dispensed.

2. The apparatus as defined in claim 1, wherein:
   each of said first and second scale means comprises a respective first and second scale ring.

3. The apparatus as defined in claim 2, wherein:
   said adjustment element comprises an adjustment knob.

4. The apparatus as defined in claim 2, wherein:
said stop means of said first scale ring is positioned thereat so as to provide a point of reference for the volume of liquid contained in the dispensing cylinder; and
the stop means of the second scale ring is positioned thereat and cooperates with the stop means of the first scale ring so as to provide a point of reference for the dispensing of the desired quantity of liquid from the dispensing cylinder.

5. The apparatus as defined in claim 2, wherein:
each of said scale rings have confronting faces structured with means providing said operable inter-engagement with one another of said first scale ring and said second scale ring.

6. The apparatus as defined in claim 5, wherein:
said operable inter-engagement-providing means comprise engageable teeth means at the confronting faces of the first scale ring and second scale ring.

7. The apparatus as defined in claim 5, wherein:
said operable inter-engagement-providing means embody respective radial tooth means provided at each of the confronting faces of the first and second scale rings.

8. The apparatus as defined in claim 5, further including:
means for resiliently biasing said second scale ring into contact with the confronting face of the first scale ring.

9. The apparatus as defined in claim 8, wherein:
said resilient biasing means comprises spring means.

10. The apparatus as defined in claim 2, wherein:
said adjustment means includes mechanism enabling free movement of said coupling element and said adjustment element when said first scale ring and second scale ring are in operable inter-engagement with one another.

11. An apparatus for dispensing a dosed quantity of a liquid from an injection device containing a dispensing cylinder, a piston arrangement displaceable at one end in the dispensing cylinder, a spindle shaft having one end connected with the other end of said piston arrangement, said dispensing apparatus comprising:

first and second scale means carried by the other end of said spindle shaft remote from said one end connected with said piston arrangement;

said first scale means indicating the volume of liquid contained in the dispensing cylinder;

said second scale means serving for dispensing a predetermined quantity of the liquid contained in the dispensing cylinder;

means for setting a desired quantity of liquid to be dispensed cooperating with said second scale means;

said setting means including structure for declutching the second scale means from the first scale means during the setting operation;

means for operating the piston arrangement for dispensing the set quantity of liquid from the cylinder; and means for interrupting the dispensing operation after there has been dispensed the set quantity of liquid from the cylinder.

* * * * *